(12) United States Patent
Goble et al.

(10) Patent No.: US 6,579,319 B2
(45) Date of Patent: Jun. 17, 2003

(54) FACET JOINT REPLACEMENT

(75) Inventors: E. Marlowe Goble, Alta, WY (US); T. Wade Fallin, Hyde Park, UT (US); Robert W. Hoy, Logan, UT (US)

(73) Assignee: MedicineLodge, Inc., Logan, UT (US)

( * ) Notice: Subject to any disclaimer, the term of this patent is extended or adjusted under 35 U.S.C. 154(b) by 0 days.

(21) Appl. No.: 09/726,169

(22) Filed: Nov. 29, 2000

(65) Prior Publication Data

US 2002/0065557 A1 May 30, 2002

(51) Int. Cl.⁷ .................................................. A61F 2/44
(52) U.S. Cl. ................................ 623/17.11; 623/17.15; 606/61
(58) Field of Search ...................... 623/16.11, 17.11, 623/17.12, 17.13, 17.14, 17.15, 17.16, 18.11; 606/60–64, 72, 73

(56) References Cited

U.S. PATENT DOCUMENTS

| | | | |
|---|---|---|---|
| 3,867,728 A | 2/1975 | Stubstad et al. | |
| 3,875,595 A | 4/1975 | Froning | |
| 4,349,921 A | 9/1982 | Kuntz | |
| 4,759,769 A | 7/1988 | Hedman et al. | |
| 4,772,287 A | 9/1988 | Ray et al. | |
| 4,863,477 A | 9/1989 | Monson | |
| 4,904,260 A | 2/1990 | Ray et al. | |
| 4,911,718 A | 3/1990 | Lee et al. | |
| 5,047,055 A | 9/1991 | Bao et al. | |
| 5,071,437 A | 12/1991 | Steffee | |
| 5,147,404 A | 9/1992 | Downey | |
| 5,171,280 A | 12/1992 | Baugartner | |
| 5,192,326 A | 3/1993 | Bao et al. | |
| 5,258,031 A | 11/1993 | Salib et al. | |
| 5,306,308 A | 4/1994 | Gross et al. | |
| 5,306,309 A | 4/1994 | Wagner et al. | |
| 5,370,697 A | 12/1994 | Baumgartner | |
| 5,401,269 A | 3/1995 | Buttner-Janz et al. | |
| 5,437,672 A | 8/1995 | Alleyne | |
| 5,458,642 A | 10/1995 | Beer et al. | |
| 5,458,643 A | 10/1995 | Oka et al. | |
| 5,514,180 A | 5/1996 | Heggeness et al. | |
| 5,527,312 A | 6/1996 | Ray | |
| 5,534,028 A | 7/1996 | Bao et al. | |
| 5,534,030 A | 7/1996 | Navarro et al. | |
| 5,545,229 A | 8/1996 | Parsons et al. | |
| 5,556,431 A | 9/1996 | Buttner-Janz | |
| 5,571,189 A | 11/1996 | Kuslich | |
| 5,571,191 A | * 11/1996 | Fitz ............................. 623/17 |
| 5,572,191 A | 11/1996 | Lundberg | |
| 5,645,597 A | 7/1997 | Krapiva | |

(List continued on next page.)

FOREIGN PATENT DOCUMENTS

| | | |
|---|---|---|
| WO | WO98/48717 A1 | 11/1998 |
| WO | WO99/23963 A1 | 5/1999 |
| WO | WO00/38582 A1 | 7/2000 |
| WO | WO 01/30248 A1 | 5/2001 |

OTHER PUBLICATIONS

Goh JC, et al., "Influence of PLIF cage size on lumbar spine stability", Spine, Jan. 2000 25:1, Medline abstract—one page.

(List continued on next page.)

Primary Examiner—Corrine McDermott
Assistant Examiner—Urmi Chattopadhyay
(74) Attorney, Agent, or Firm—Pandiscio & Pandiscio

(57) ABSTRACT

A prosthesis for the replacement of a diseased or traumatized facet of a mammalian vertebra includes a surface that articulates with another prosthetic facet or a natural facet, a portion that replaces at least a bony portion of the diseased or traumatized spine facet which is to be replaced, and an element to attach the prosthesis to the vertebra in a manner that does not require attachment to or abutment against the posterior arch. A method of installing the prosthesis includes the steps of resecting at least a portion of a facet and attaching the prosthesis in a manner that does not require attachment or abutment against the posterior arch.

10 Claims, 17 Drawing Sheets

U.S. PATENT DOCUMENTS

| | | |
|---|---|---|
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,702,450 A | 12/1997 | Bisserie |
| 5,716,415 A | 2/1998 | Steffee |
| 5,824,093 A | 10/1998 | Ray et al. |
| 5,824,094 A | 10/1998 | Serhan et al. |
| 5,865,846 A | 2/1999 | Bryan et al. |
| 5,868,745 A | 2/1999 | Alleyne |
| 5,893,889 A | 4/1999 | Harrington |
| 6,001,130 A | 12/1999 | Bryan et al. |
| 6,014,588 A | 1/2000 | Fitz |
| 6,019,792 A | 2/2000 | Cauthen |
| 6,039,763 A | 3/2000 | Shelokov |
| 6,063,121 A | 5/2000 | Xavier et al. |
| 6,066,325 A | 5/2000 | Wallace et al. |
| RE36,758 E | 6/2000 | Fitz |
| 6,080,157 A | 6/2000 | Cathro et al. |
| 6,113,637 A | 9/2000 | Gill et al. |
| 6,132,464 A | 10/2000 | Martin |
| 6,132,465 A | 10/2000 | Ray et al. |

OTHER PUBLICATIONS

Head WC, "Wagner surface replacement arthroplasty of the hip. Analysis of fourteen failures in forty–one hips", J Bone Joint Surg. [AM], Mar. 1981 63:3, Medline abstract—one page.

Khoo LT, et al., "A Biomechanical Analysis of the Effects of Lumbar Fusion on the Adjacent Vertebral Motion Segment", Proceedings of the 2000 Annual Meeting of the North American Spine Society, New Orleans.

Kotani Y, et al., "The effects of spinal fixation and destabilization on the biomechanical and histologic properties of spinal ligaments. An in vivo study.", Spine, Mar. 15, 1998 23:6, Medline abstract—one page.

Lemaire JP, et al., "Intervertebral Disc Prosthesis: Results and Prospects for the year 2000", Clinical Orthopaedics and Related Research, No. 337, pp. 64–76.

Nagata H, et al., "The effects of immobilization of long segments of the spine on the adjacent and distal facet force and lumbrosacral motion", Spine, Dec. 1993, 18:16, pp. 2471–2479.

Nibu K, et al., "Multidirectional stabilizing potential of BAK interbody spinal fusion system for anterior surgery [see comments]", J Spinal Discord, Aug. 1997, 10:4, Medline abstract—one page.

Tsantrizos A, et al., "Segmental stability and compressive strength of posterior lumbar interbody fusion implants", Spine, Aug. 1, 2000 25:15, Medline abstract—one page.

M.A. Reiley, U.S. Patent Application Publication No. US 2002/0123806 A1, published Sep. 5, 2002.

* cited by examiner

FACET JOINT REPLACEMENT

BACKGROUND OF THE INVENTION

1. Field of the Invention

The present invention relates to surgical devices and methods to replace a damaged, diseased, or otherwise painful spinal facet joint.

2. Description of Related Art

Traumatic, inflammatory, metabolic, synovial, neoplastic, and degenerative disorders of the spine can produce debilitating pain that can have severe socioeconomic and psychological effects. One of the most common surgical interventions today is arthrodesis, or spine fusion, of one or more motion segments, with approximately 300,000 procedures performed annually in the United States. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it is believed that spine fusion creates increased stresses and, therefore, accelerated degeneration of adjacent non-fused motion segments. Additionally, pseudoarthrosis, as a result of an incomplete or ineffective fusion, may reduce or even eliminate pain relief for the patient. Finally, the fusion device, whether artificial or biological, may migrate out of the fusion site.

Recently, several attempts have been made to recreate the natural biomechanics of the spine by use of an artificial disc. Artificial discs provide for articulation between vertebral bodies to recreate the full range of motion allowed by the elastic properties of the natural intervertebral disc which directly connects two opposed vertebral bodies.

However, the artificial discs proposed to date do not fully address the mechanics of motion of the spinal column. In addition to the intervertebral disc, posterior elements called the facet joints help to support axial, torsional and shear loads that act on the spinal column. Furthermore, the facet joints are diarthroidal joints that provide both sliding articulation and load transmission features. The effects of their absence as a result of facetectomy is believed to produce significant decreases in the stiffness of the spinal column in all planes of motion: flexion and extension, lateral bending, and rotation. Furthermore, contraindications for artificial discs include arthritic facet joints, absent facet joints, severe facet joint tropism or otherwise deformed facet joints.

U.S. Pat. No. Re. 36,758 to Fitz discloses an artificial facet joint where the inferior facet, the mating superior facet, or both, are covered with a cap. The cap requires no preparation of the bone or articular surfaces; it covers and, therefore, preserves the bony and articular structure.

The capping of the facet has several potential disadvantages. If the facet joint is osteoarthritic, a cap will not remove the source of the pain. Additionally, at least in the case of surface replacements for osteoarthritis femoral heads, the capping of articular bone ends has proven to lead to clinical failure by means of mechanical loosening. The clinical failure is hypothesized to be a sequela of disrupting the periosteum and ligamentum teres femoris, both serving a nutrition delivery role to the femoral head, thereby leading to avascular necrosis of the bony support structure for the surface replacement. Another potential disadvantage is that in order to accommodate the wide variability in anatomical morphology of the facets, not only between individuals but also between levels within the spinal column, a very wide variety of sizes and shapes would be required.

U.S. Pat. No. 6,132,464 to Martin discloses a spinal facet joint prosthesis that is supported on the lamina, or the posterior arch of the vertebra. Extending from this support structure are inferior and/or superior blades that replace the cartilage at the facet joint. Like the Fitz design, the Martin prosthesis generally preserves existing bony structures and therefore does not address pathologies which affect the bone of the facets in addition to affecting the associated cartilage. Furthermore, the Martin invention requires a mating condition between the prosthesis and the lamina, or the posterior arch, that is a thin base of curved bone that carries all four facets and the spinous process. Since the posterior arch is a very complex and highly variable anatomic surface, it would be very difficult to design a prosthesis that provides reproducible positioning to correctly locate the cartilage-replacing blades for the facet joints.

Another approach to surgical intervention for spinal facets is provided in WO9848717A1 to Villaret. While Villaret teaches the replacement of spine facets, the replacement is interlocked in a manner to immobilize the joint.

Facet joint replacement in conjunction with artificial disc replacements represent a unique solution to recreating a fully functional motion segment that is compromised due to disease or trauma. Together, facet joint and disc replacement can eliminate all sources of pain, return full function and range of motion, and completely restore the natural biomechanics of the spinal column. Additionally, degenerative or traumatized facet joints may be replaced in the absence of disc replacement when the natural intervertebral disc is unaffected by the disease or trauma.

It would therefore be an improvement in the art to provide a vertebral facet replacement device and method that replaces a bony portion of the facets so as to remove the source of arthritic, traumatic, or other disease mediated pain.

SUMMARY OF THE INVENTION

It is an object of the invention to provide an artificial vertebral facet that replaces the cartilage and a portion of the bone of a facet.

It is a further object of the invention to provide a method for preparing a facet for the installation of an artificial vertebral facet.

It is another object to provide a method for replacing a spinal facet.

It is yet another object of the invention to provide a total vertebral facet joint replacement.

In the preferred embodiment, an inferior facet of a superior vertebra is resected at the base of the facet where it connects to the posterior arch. The fin of a prosthetic inferior facet is pressed into the interior bone space of the posterior arch. Alternatively, a tool, such as a broach or punch, may be used to first prepare a space for the fin within the posterior arch.

Alternatively, or in addition, a superior facet of an inferior vertebra that articulates with the inferior facet is resected at the base of the facet where it connects to the pedicle. The post of a prosthetic superior facet is pressed into the interior bone space of the pedicle. Alternatively, a tool, such as a broach or punch, may be used to first prepare a space for the post within the pedicle.

The post and the fin may be porous coated to promote bone ingrowth in order to achieve long term fixation. Acute fixation is provided by a press fit between the post or fin and the internal surface of the bone. The porous coating may carry osteoconductive agents, such as hydroxylapatite, calcium sulfate, or demineralized bone matrix. Alternatively, the porous coating may carry osteoinductive agents, such as bone morphogenic proteins, including rhBMP-2 and rhBMP-7.

Another embodiment of the present invention provides a flange extending from the prosthetic facet. The flange is oriented relative to the body of the prosthesis such that when the flange is placed against the pedicle and in a manner such that the planar surface of the flange is perpendicular to the axis of the pedicle interior bone canal, the articulating surface of the prosthesis will be properly positioned to match the articulating surface of the natural facet. The flange includes a hole for the passage of a fastener to securely attach the prosthesis to the pedicle. The fastener can be a screw, spike, tack, staple, or the like.

Because the present invention allows for the individual replacements of facets, only compromised facets need be replaced. For example, if only one facet is affected by disease or trauma, it can be resected and replaced with a facet prosthesis that articulates with an opposing natural facet.

The present invention has numerous advantages over the prior art. One advantage is that the quality of attachment of the prosthesis is improved. The present invention provides a precise and tight press fit into bones, as opposed to relying on prosthetic surfaces mating with highly complex and variable external surfaces of the vertebra, such as the posterior arch or facet. Another advantage is that the optional porous coating is placed into interior bone spaces where porous coatings have proven to achieve bone ingrowth for excellent long term fixation strength. This ability to achieve bone ingrowth is uncertain for the prior art devices that engage the external bone surfaces of the vertebra. Yet another advantage lies in the removal of the facet bone structure; where the facet bone is involved in the disease pathology or the trauma that compromised the articular or cartilaginous surface of the facet, resection provides a means for ensuring that all pain associated with the disease or trauma is removed and the true joint line is restored. With prior art devices, the bony structure of the facets was generally left intact.

The above, and other objects, features and advantages of the present invention, will become apparent from the following description which is to be read in conjunction with the accompanying drawings.

DETAILED DESCRIPTION OF THE PREFERRED EMBODIMENTS

Figure 1:
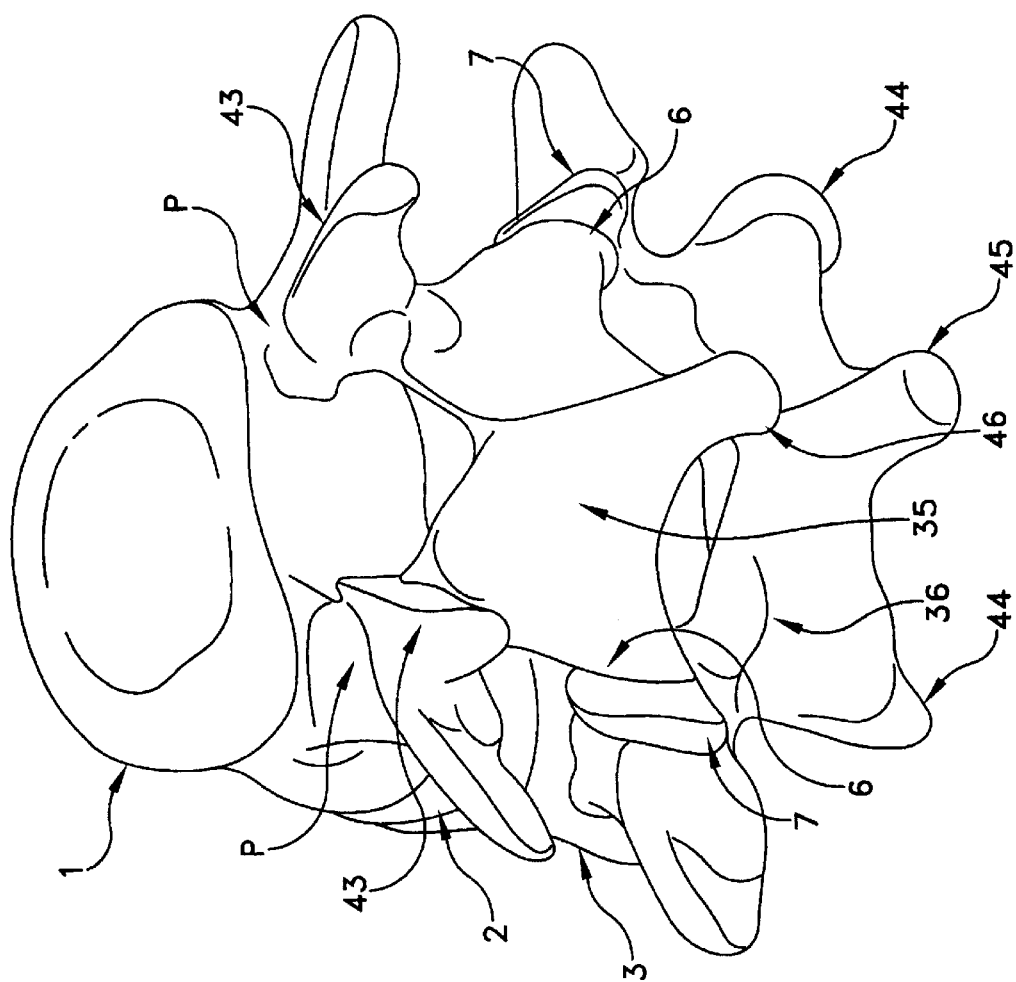
FIG. 1 is a perspective view of a portion of the spine.
Figure 1A:
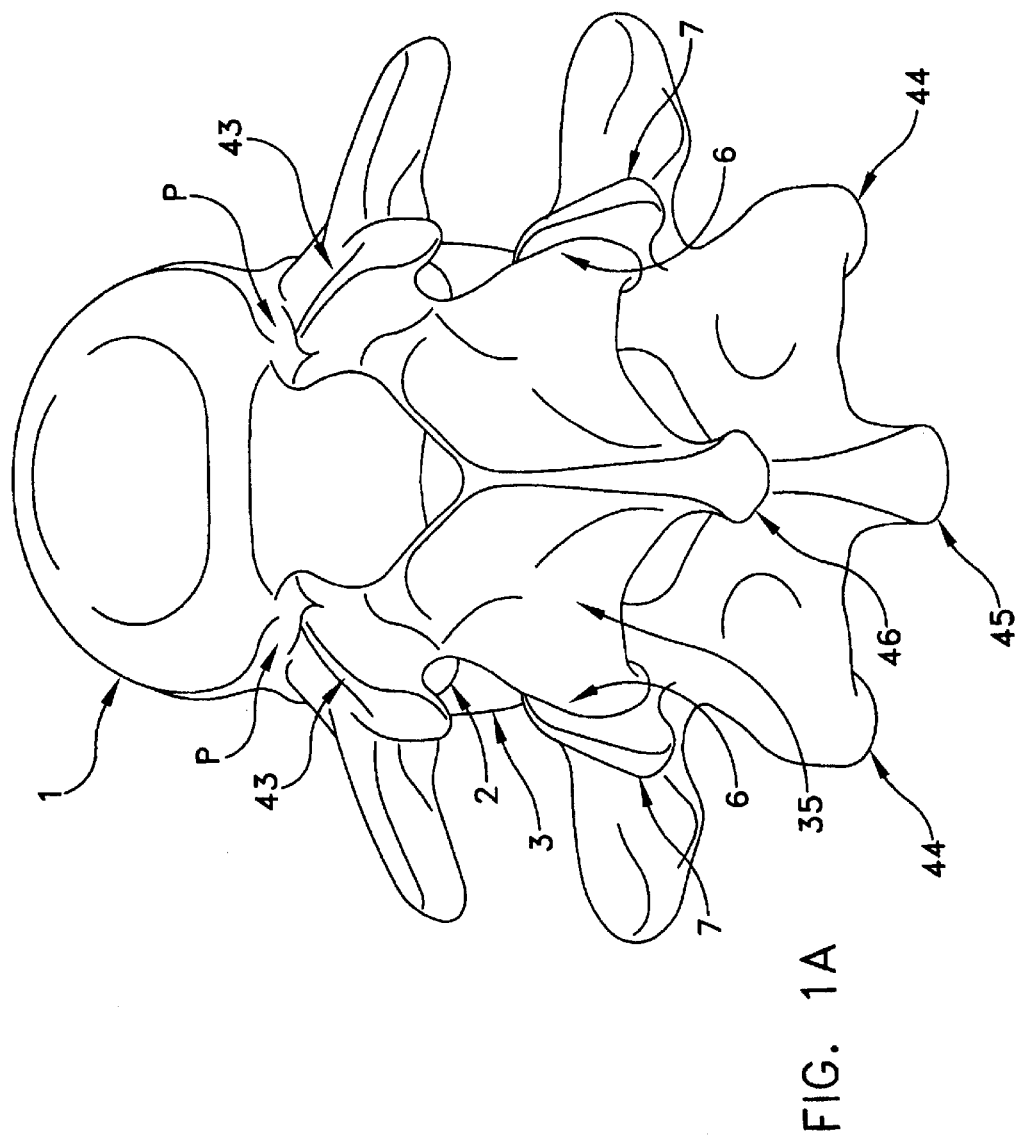
FIG. 1A is a dorsal view of the portion of the spine shown in FIG. 1.

Referring now to FIGS. 1 and 1A, there is shown a superior vertebra 1 and an inferior vertebra 3, with an intervertebral disc 2 located in between. Vertebra 1 has superior facets 43, inferior facets 6, posterior arch 35 and spinous process 46. Vertebra 3 has superior facets 7, inferior facets 44, posterior arch 36 and spinous process 45.

Figure 2:
FIG. 2 is a lateral view of a facet joint reconstructed in accordance with the present invention.

Referring now to FIG. 2, the left inferior facet 6 of vertebra 1 has been resected and an inferior facet prosthesis 4 has been attached to vertebra 1. Similarly, the left superior facet of vertebra 3 has been resected and a superior facet prosthesis 5 has been attached to vertebra 3.

Figure 3:
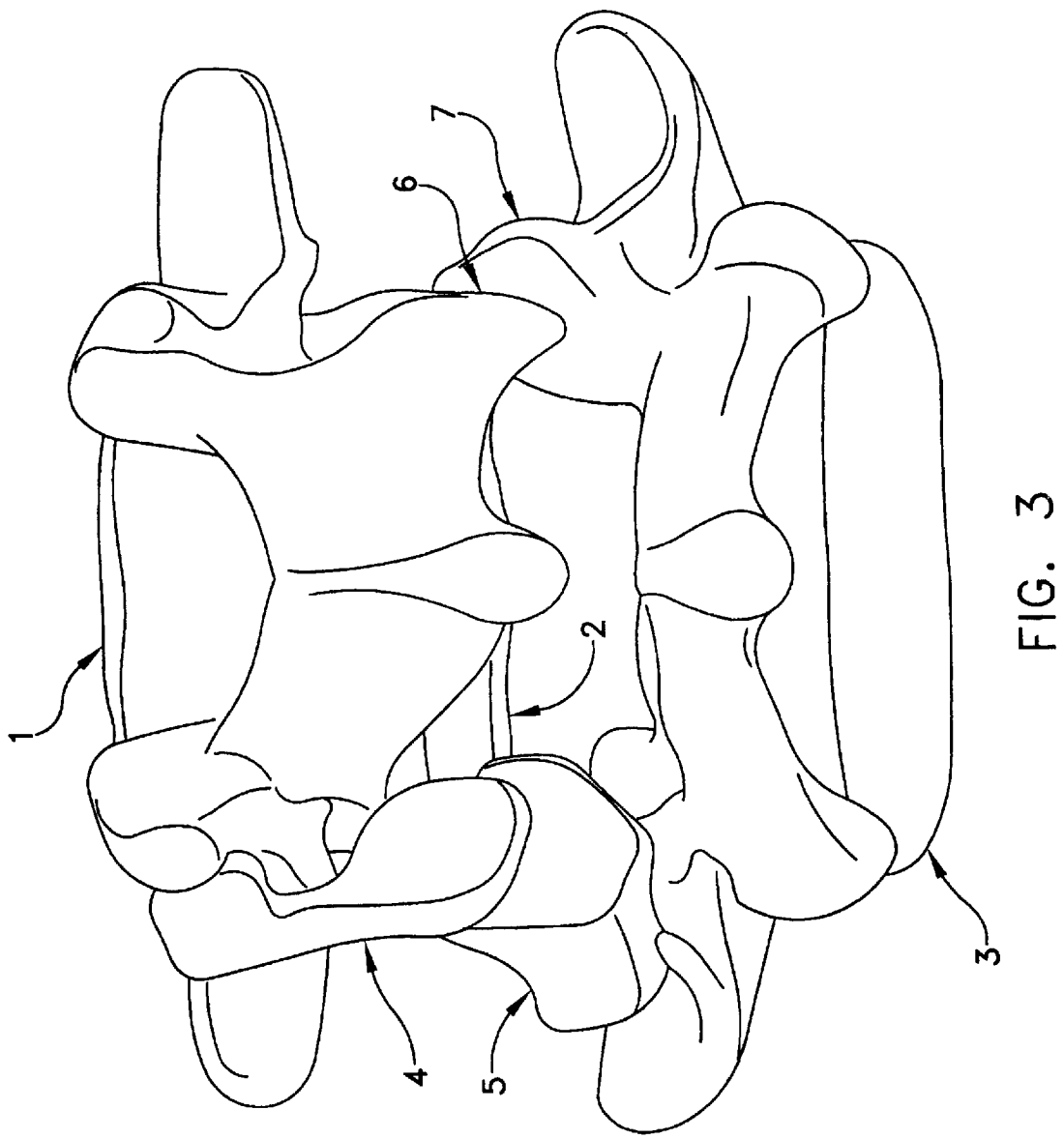
FIG. 3 is a dorsal view of the facet joint shown in FIG. 2.

FIG. 3 illustrates a dorsal view of the elements shown in 2. It can be appreciated that inferior facet prosthesis 4 replicates the natural anatomy when compared to the contralateral inferior facet 6 of vertebra 1. Similarly, it can be appreciated that superior facet prosthesis 5 replicates the natural anatomy when compared to the contralateral superior facet 7 of vertebra 3.

Figure 4:
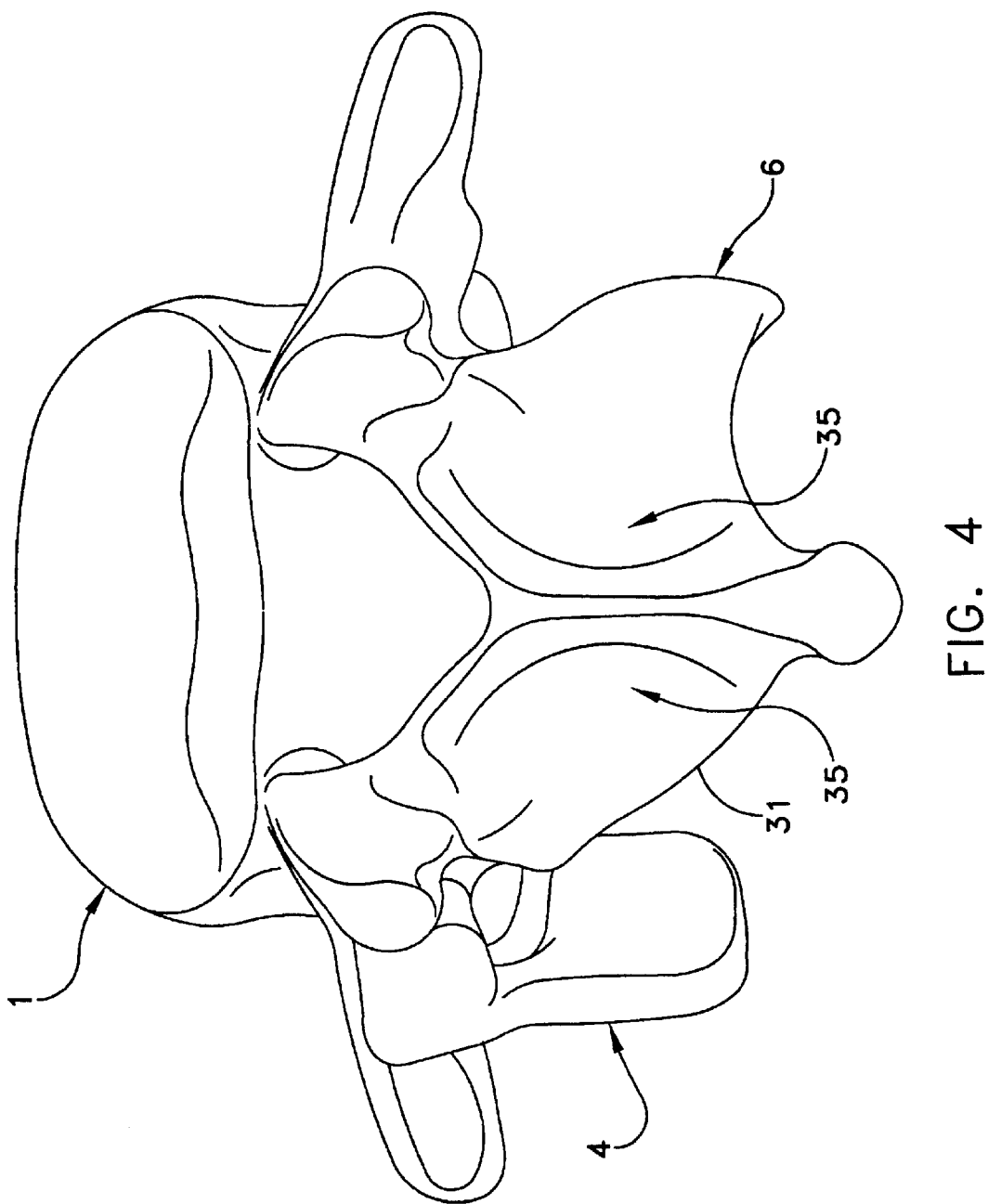
FIG. 4 is a perspective view of the implanted left inferior facet prosthesis shown in FIGS. 2 and 3.

Turning now to FIG. 4, a perspective view of vertebra 1 with implanted inferior facet prosthesis 4 is provided. Resection at 31 has removed the natural inferior facet 6 at the bony junction between the inferior facet 6 and the posterior arch 35. In this manner, any bone pain associated with a disease, such as osteoarthritis, or trauma will be eliminated as the involved bony tissue has been osteotomized.

Figure 5:
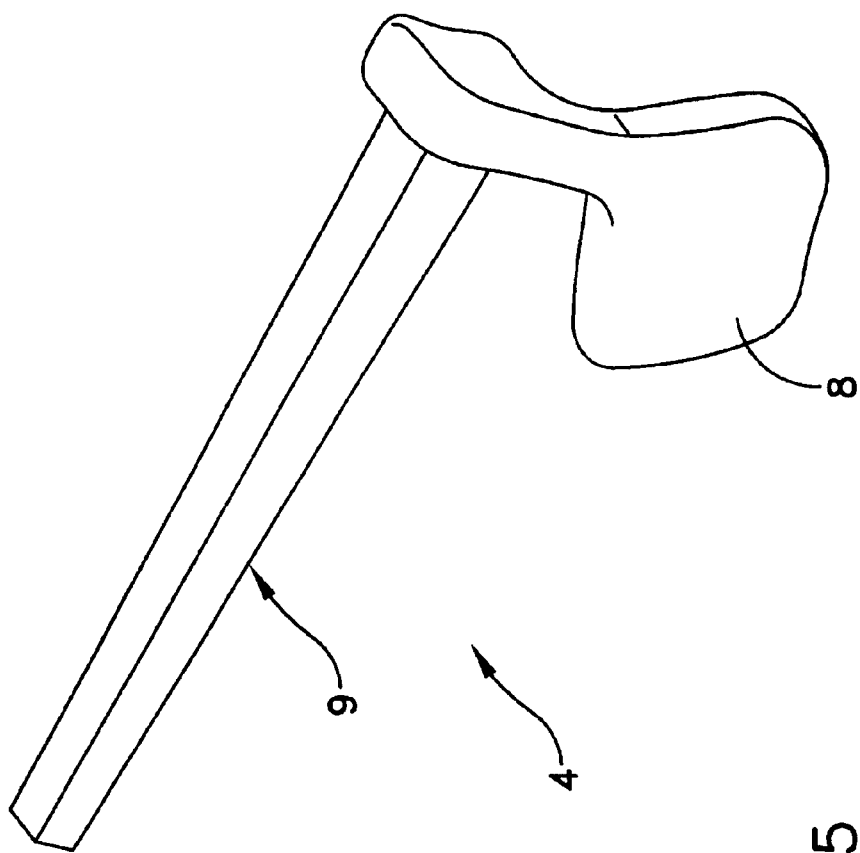
FIG. 5 is a perspective view of the left inferior facet prosthesis shown in FIGS. 2 and 3.

FIG. 5 illustrates a perspective view of inferior facet prosthesis 4. Surface 8 replicates the natural articular surface of the replaced inferior facet 6. Post 9 provides a means to affix inferior facet prosthesis 4 to vertebra 1. Post 9 is implanted into the interior bone space of the left pedicle P (FIG. 6) on vertebra 1 and may or may not extend into the vertebral body of vertebra 1 to provide additional stability.

Figure 6:
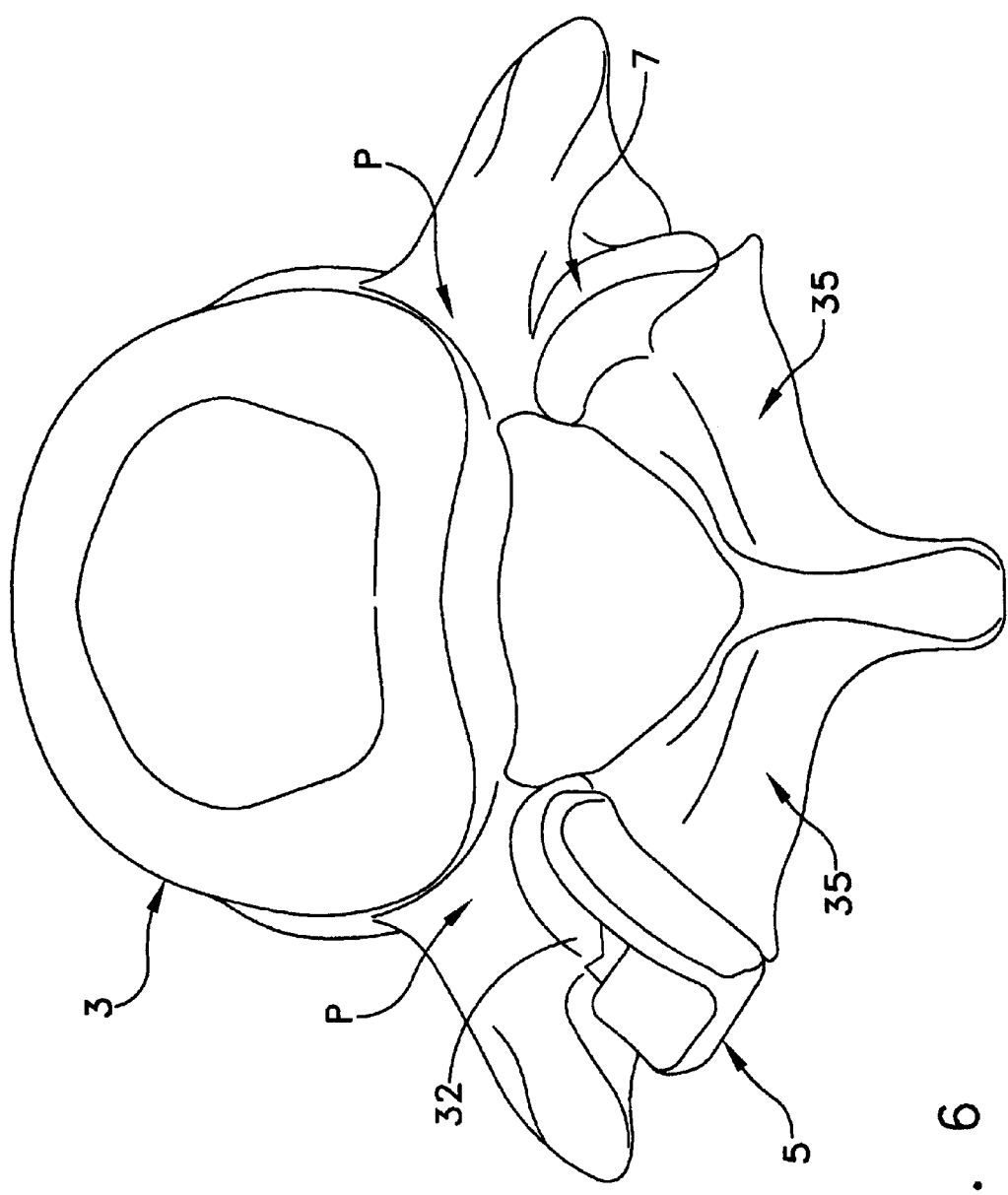
FIG. 6 is a cranial view of the implanted left superior facet prosthesis shown in FIGS. 2 and 3.

FIG. 6 illustrates a cranial view of vertebra 3 with implanted superior facet prosthesis 5. Resection surface 32 represents the bony junction between the natural superior facet and the posterior arch 35.

Figure 7:
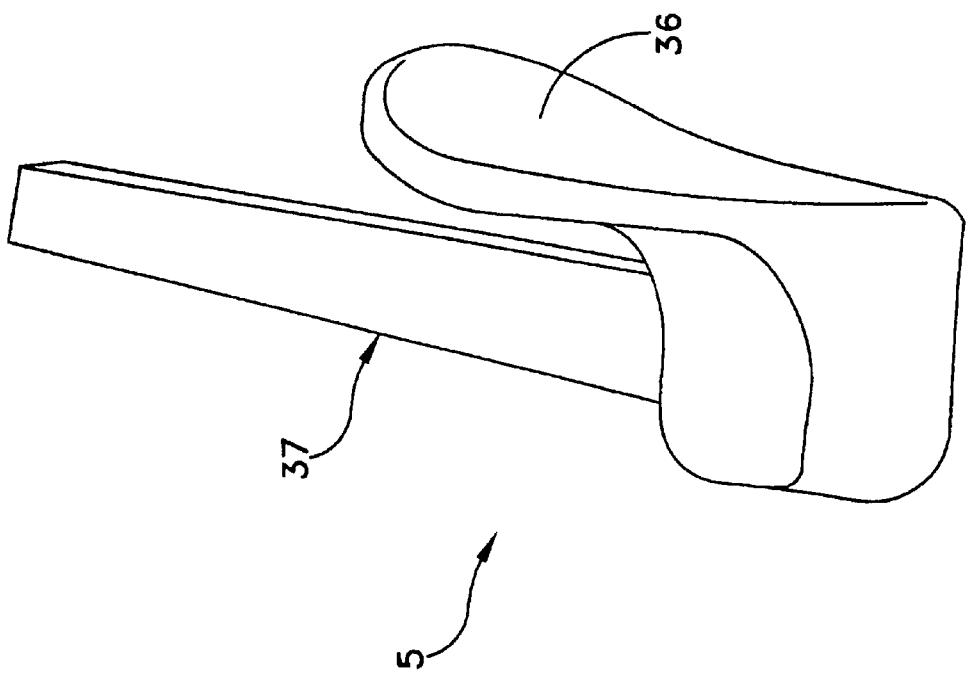
FIG. 7 is a perspective view of the left superior facet prosthesis shown in FIGS. 2 and 3.

FIG. 7 illustrates a perspective view of superior facet prosthesis 5. Surface 36 replicates the natural articular surface of the replaced superior facet 7. Post 37 provides a means for affixing superior facet prosthesis 5 to vertebra 3. Post 37 is implanted into the interior bone space of the left pedicle P (FIG. 6) on vertebra 3 and may or may not extend into the vertebral body of vertebra 3 to provide additional stability.

When the total facet joint is replaced, as shown in FIGS. 2 and 3, then surface 8 (FIG. 5) articulates with surface 36 (FIG. 7) to recreate the natural biomechanics of the spine motion segment made up of vertebra 1, vertebra 3, and intervertebral disc 2.

Figure 8:
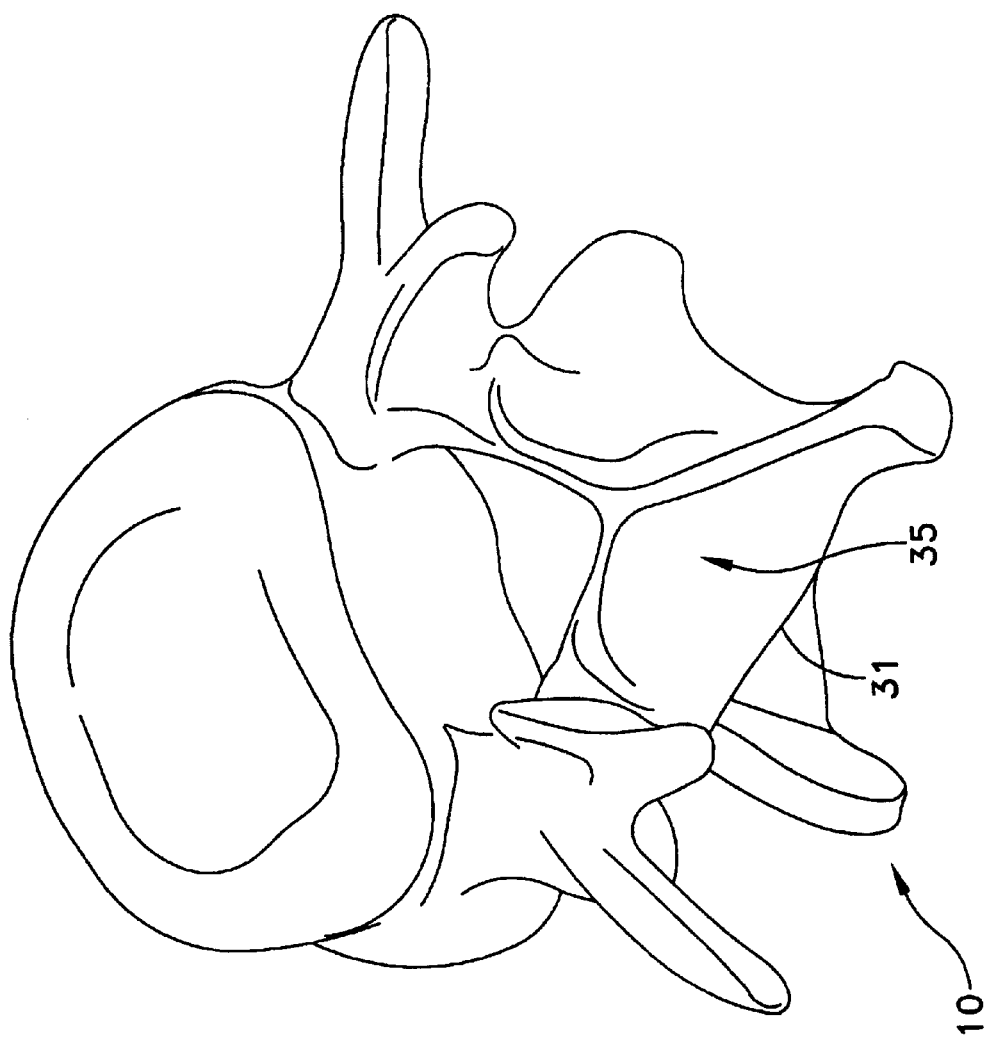
FIG. 8 is a perspective view of an alternate implanted left superior facet prosthesis.

FIG. 8 illustrates an alternative inferior facet prosthesis 10 which is implanted into the interior bone space of posterior arch 35. The interior bone space is accessed from the resection 31.

Figure 9:
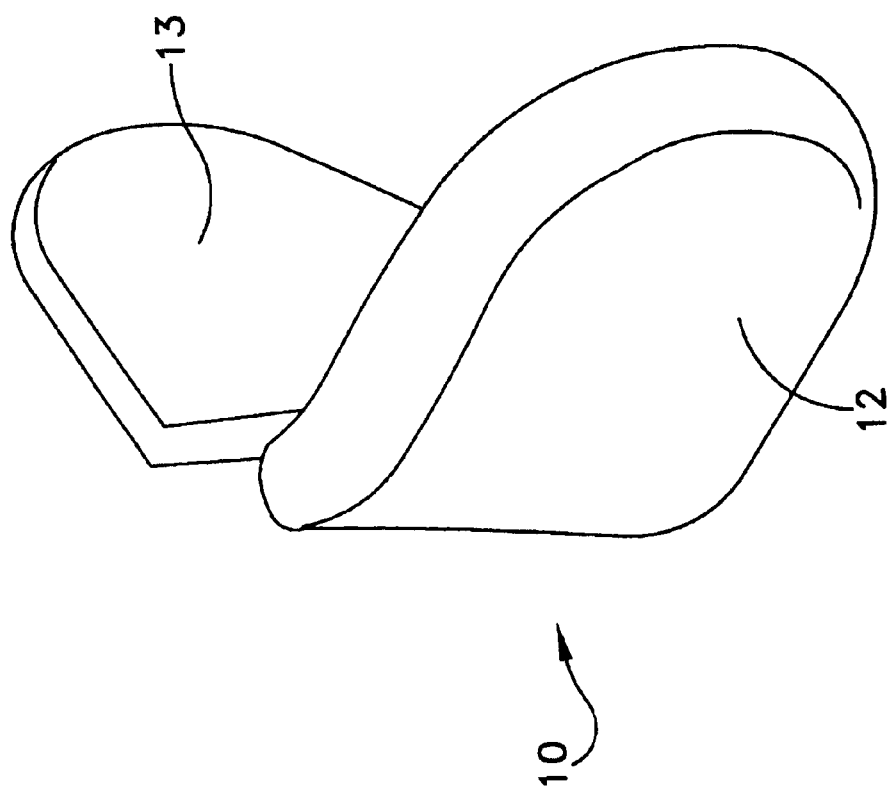
FIG. 9 is a perspective view of an alternate left superior facet prosthesis.

FIG. 9 shows details of alternative inferior facet prosthesis 10, including the fin 13 that extends into the interior bone space of posterior arch 35. Surface 12 replicates the natural articular surface of the replaced facet.

If desired, a corresponding fin construction can be used to form a prosthetic superior facet.

The surfaces of post 9 (FIG. 5), post 37 (FIG. 7) and fin 13 (FIG. 9) may or may not include porous coatings to facilitate bone ingrowth to enhance the long term fixation of the implant. Furthermore, such porous coatings may or may not include osteoinductive or osteoconductive substances to further enhance the bone remodeling into the porous coating.

Figure 10:
FIG. 10 is a lateral view of an alternative reconstructed facet joint.

Referring now to FIG. 10, there is shown a lateral view of a superior vertebra 14 and an inferior vertebra 16, with an intervertebral disc 15 located in between is shown. The left inferior facet of vertebra 14 has been resected and an inferior facet prosthesis 18 has been attached to vertebra 14 by means of a screw fastener 17, wherein the screw fastener is implanted into an interior bone space of the pedicle of the vertebra. Similarly, the left superior facet of vertebra 16 has been resected and a superior facet prosthesis 19 has been attached to vertebra 16 by means of a screw fastener 17, wherein the screw fastener is implanted into an interior bone space of the pedicle of the vertebra.

Figure 11:
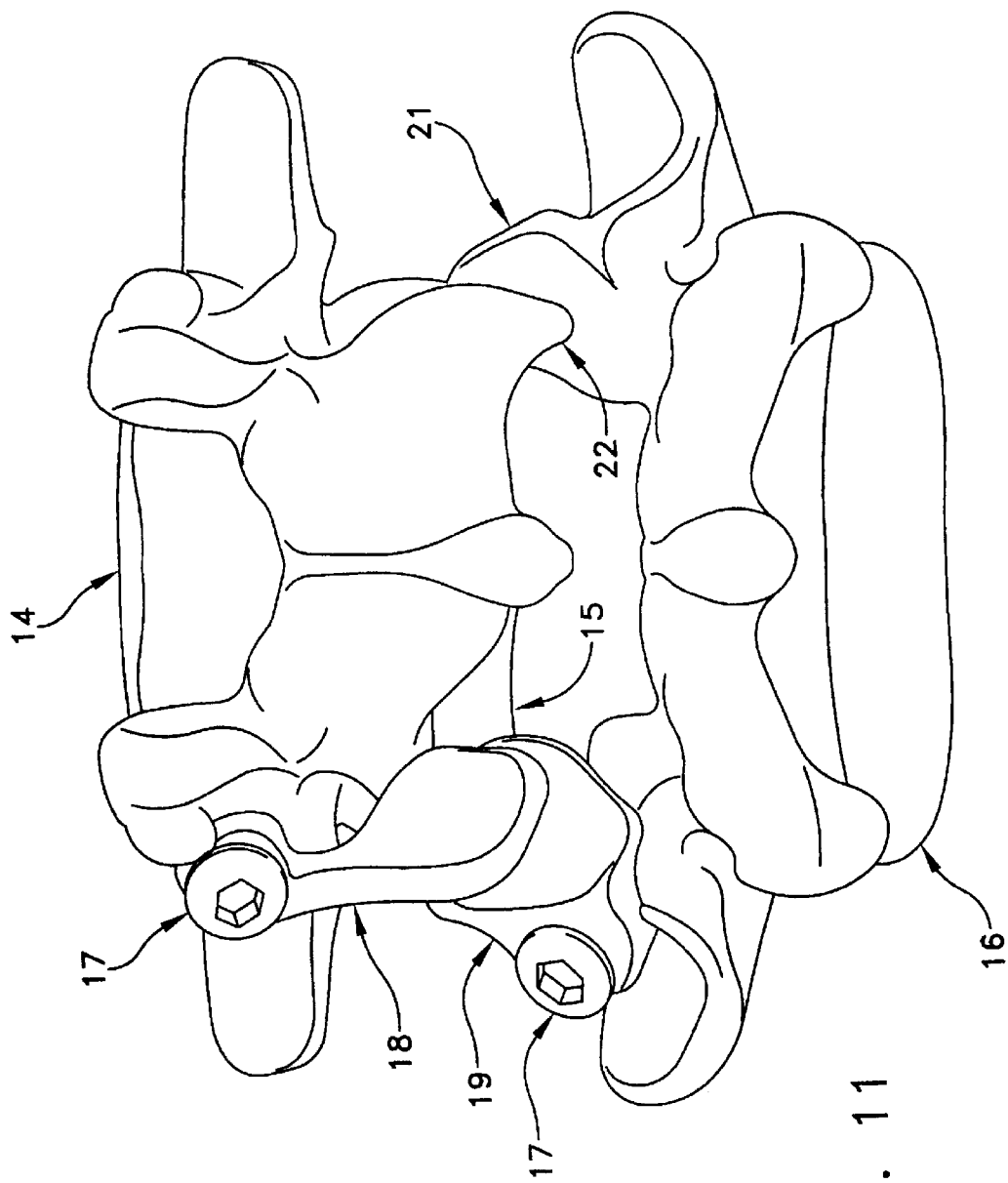
FIG. 11 is a dorsal view of an alternative reconstructed facet joint.

FIG. 11 illustrates a dorsal view of the elements of FIG. 10. It can be appreciated that inferior facet prosthesis 18 replicates the natural anatomy when compared to the contralateral inferior facet 22 of vertebra 14. Similarly, it can be appreciated that superior facet prosthesis 19 replicates the natural anatomy when compared to the contralateral superior facet 21 of vertebra 16. In a preferred embodiment of the present invention, inferior facet prosthesis 18 and/or superior facet prosthesis 19 has a bone contacting surface which is porous coated to allow for bone ingrowth.

Figure 12:
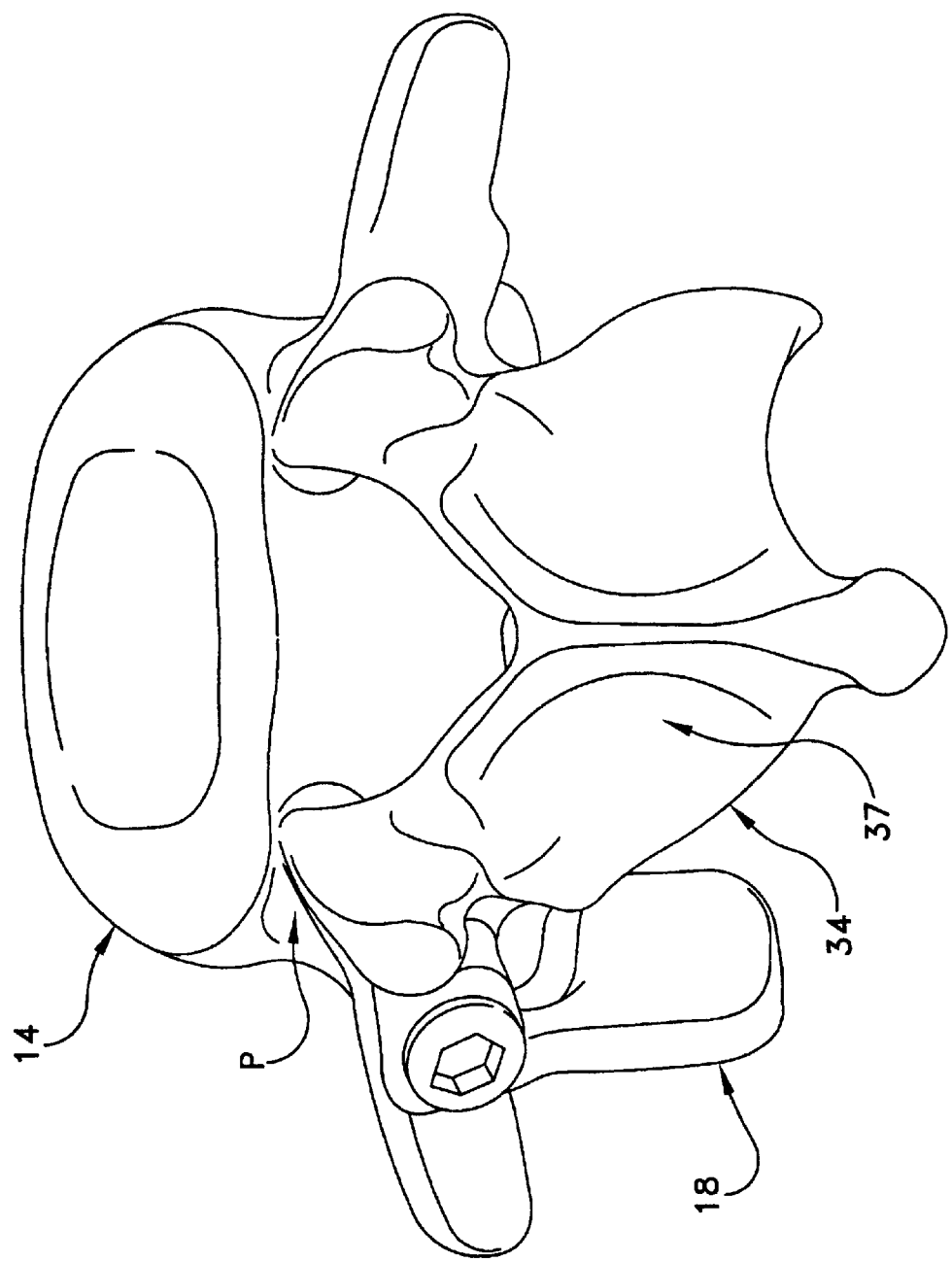
FIG. 12 is a perspective view of the implanted left inferior facet prosthesis shown in FIGS. 10 and 11.

Turning now to FIG. 12, there is provided a perspective view of vertebra 14 with implanted inferior facet prosthesis 18. Resection 34 has removed the natural inferior facet at the bony junction between the inferior facet and the posterior arch 37. In this manner, any bone pain associated with a disease, such as osteoarthritis, or trauma will be eliminated inasmuch as the involved bony tissue has been osteotomized.

Figure 13:
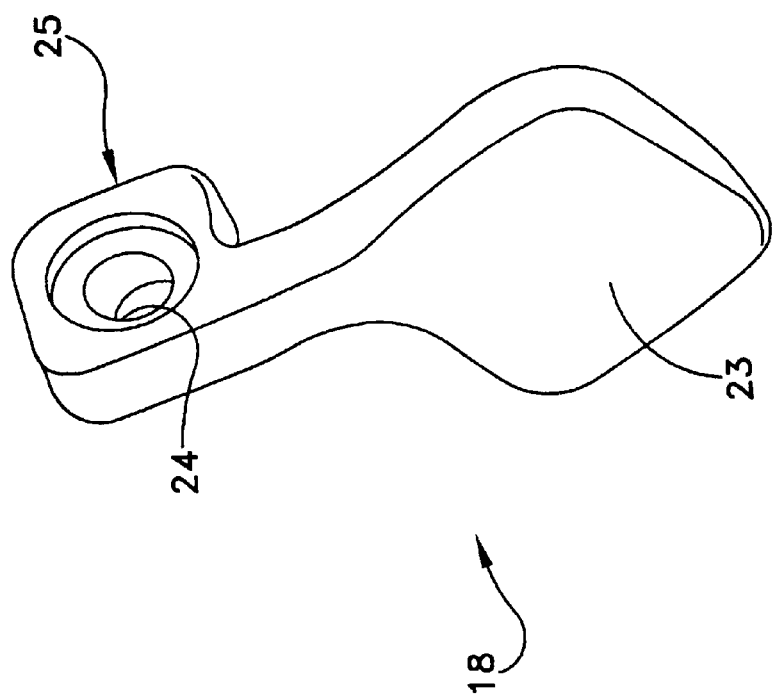
FIG. 13 is a perspective view of the alternative left inferior facet prosthesis shown in FIGS. 10 and 11.

FIG. 13 illustrates a perspective view of inferior facet prosthesis 18. Surface 23 replicates the natural articular surface of the replaced facet. Flange 25 contacts the pedicle and hole 24 receives a fastener to attach inferior facet prosthesis 18 to vertebra 14.

Figure 14:
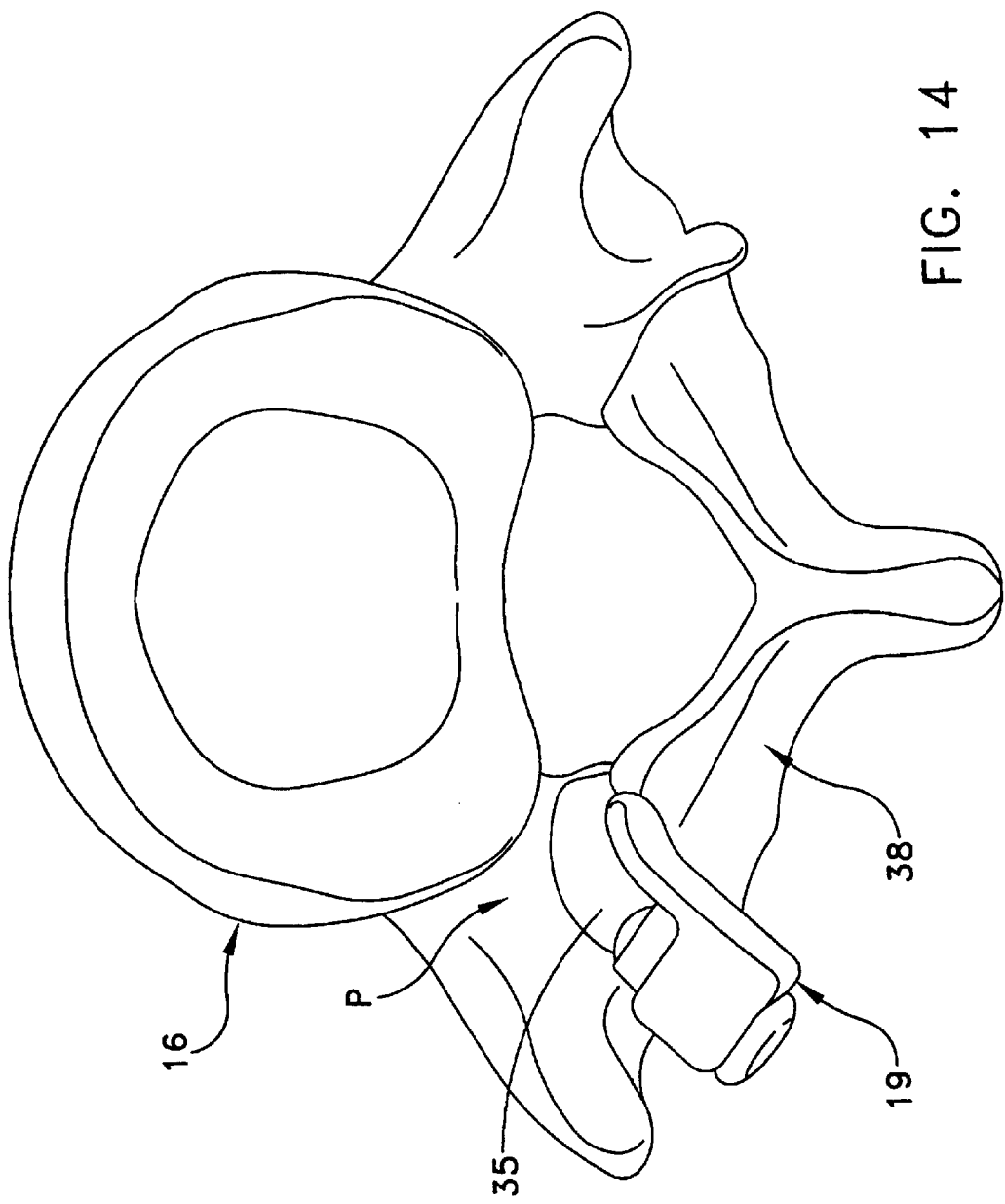
FIG. 14 is a cranial view of the alternative implanted left superior facet prosthesis shown in FIGS. 10 and 11.

FIG. 14 illustrates a cranial view of vertebra 16 with implanted superior facet prosthesis 19. Resection surface 35 represents the bony junction between the natural superior facet and the posterior arch 38.

Figure 15:
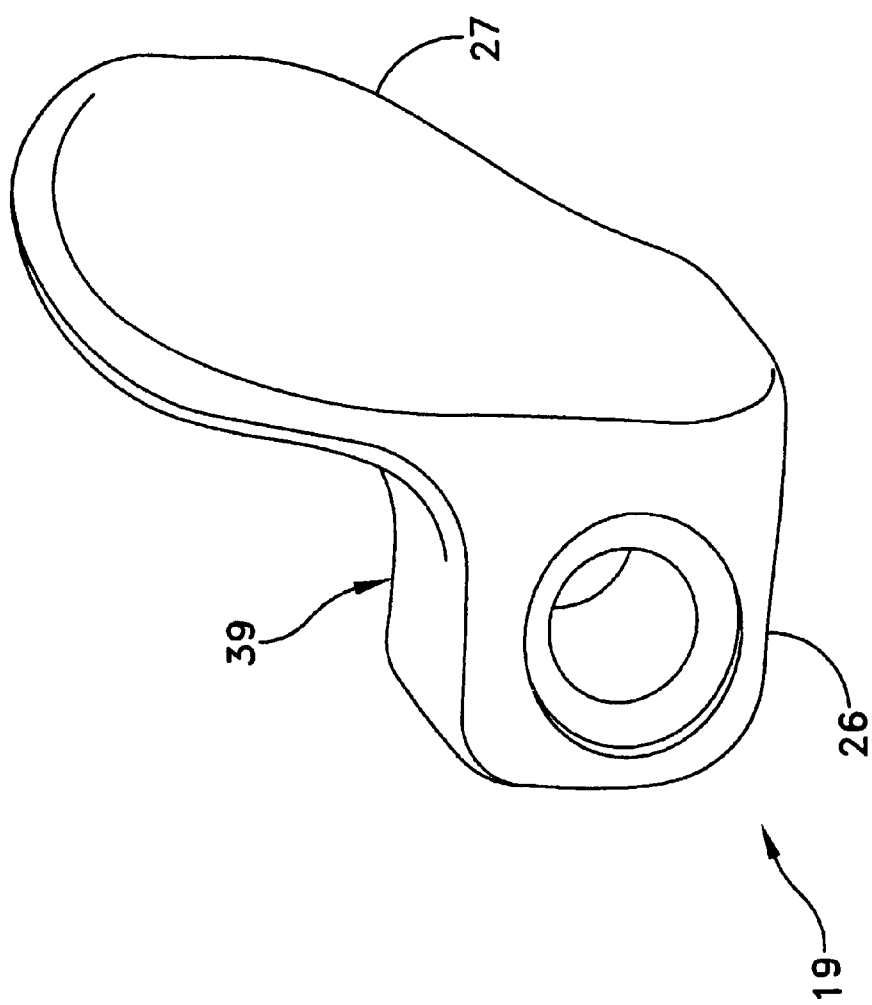
FIG. 15 is a perspective view of the alternative left superior facet prosthesis shown in FIGS. 10 and 11.

FIG. 15 illustrates a perspective view of superior facet prosthesis 19. Surface 27 replicates the natural articular surface of the replaced facet. Flange 39 contacts the pedicle and hole 26 receives a fastener to attach inferior facet prosthesis 19 to vertebra 16.

Figure 16:
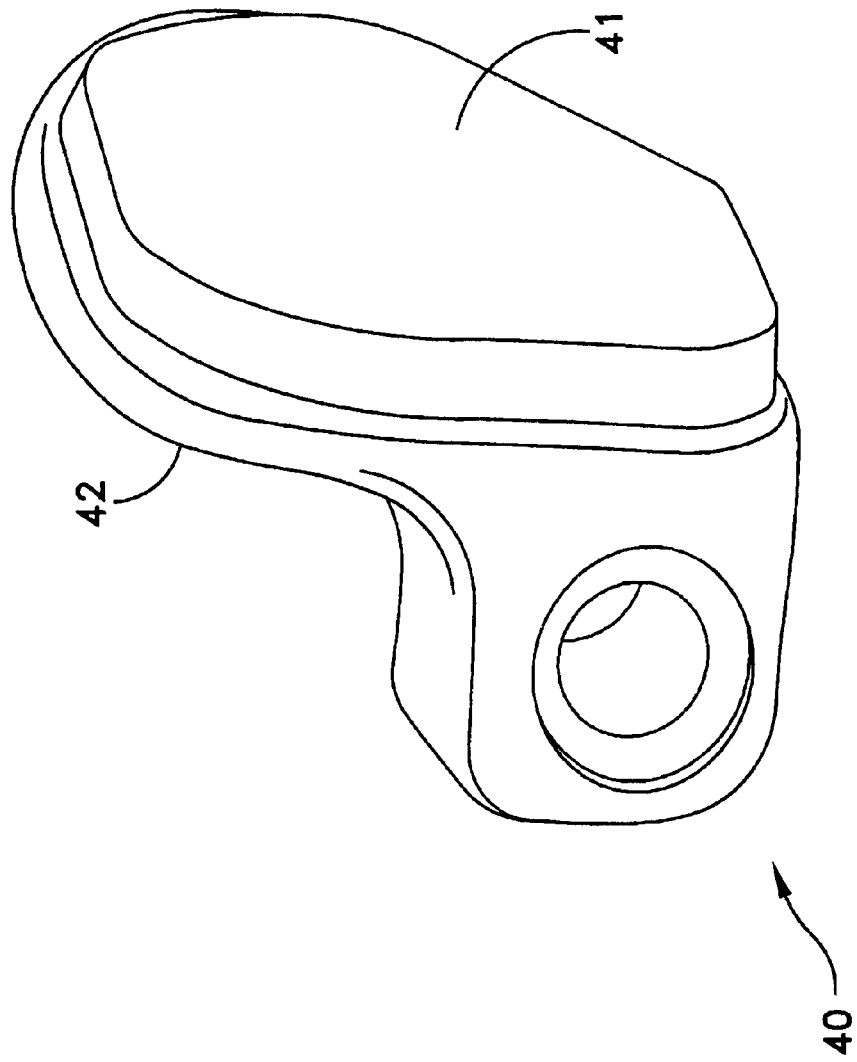
FIG. 16 is a perspective view of an alternate bearing surface for the superior facet prosthesis shown in FIG. 15.

FIG. 16 illustrates an alternative superior facet prosthesis 40 with an bearing surface 41 that mounts to substrate 42. The bearing surface 41 is a biocompatible polymeric material, such as ultra high molecular weight polyethylene. Alternately, the bearing surface can be ceramic, such as zirconia or alumina, or metal. The substrate is a biocompatible metal alloy, such as an alloy of titanium, cobalt, or iron.

Having described preferred embodiments of the invention with reference to the accompanying drawings, it is to be understood that the embodiments shown herein are by way of example, and that various changes and modifications may be effected by one skilled in the art without departing from the scope or spirit of the invention as defined in the following claims.

What is claimed is:

1. A prosthesis for the replacement of at least a portion of the bone of a facet located on a mammalian vertebra, comprising:

a surface that articulates with another facet;

a bone contacting surface that contacts one of an exterior surface or a resected surface of said vertebra, said surface that articulates being connected to said bone contacting surface;

a fixation element that attaches said bone contacting surface to said vertebra, said fixation element being adapted for implantation into an interior bone space of a pedicle of said vertebra;

and wherein said prosthesis is configured so that no portion of said prosthesis contacts the posterior arch of said vertebra.

2. The device of claim 1 wherein said fixation element is a screw.

3. The device of claim 1 wherein said surface that articulates is connected to said bone contacting surface that contacts one of said exterior surface or said resected surface of said vertebra, wherein said bone contacting surface is porous coated to allow for bone ingrowth.

4. A prosthesis for the replacement of at least a portion of the bones of opposed and articulating facets located on a mammalian vertebra, comprising:

an inferior component adapted to be attached to a first vertebra; and a superior component adapted to be attached to a second vertebra;

where the first vertebra is adjacent and superior to the second vertebra; and where one of said inferior and superior components includes:

a flange that connects to one of an exterior surface or a resected surface of said vertebra; and a fixation element that attaches said flange to said vertebra, said fixation element being adapted for implantation into an interior bone space of a pedicle of said vertebra;

and further wherein said prosthesis is configured so that no portion of said prosthesis contacts the posterior arch of said vertebra.

5. A prosthesis according to claim 4 wherein said fixation element is a screw.

6. A method for replacing a facet of a mammalian vertebra, comprising the steps of:

resecting at least a portion of the bone of said facet;

attaching a prosthetic facet to the remaining bone of said vertebra with a fixation element implanted into an interior bone space of a pedicle of said vertebra such that no portion of the prosthetic facet contacts the posterior arch of said vertebra;

where said prosthetic facet is adapted to articulate with another facet.

7. A prosthesis according to claim 6 wherein said fixation element is a screw.

8. A method for replacing a facet joint of a mammalian spine, comprising the steps of:

resecting at least a portion of the bone of a first facet on a first vertebra;

attaching a first prosthetic facet to the remaining bone of said first vertebra with a first fixation element implanted into an interior bone space of a pedicle of said first vertebra such that no portion of said prosthetic facet contacts the posterior arch of said vertebra;

resecting at least a portion of the bone of a second facet on a second vertebra; and attaching a second prosthetic facet to the remaining bone of said second vertebra with a second fixation element implanted into an interior bone space of a pedicle of said second vertebra such that no portion of said prosthetic facet contacts the posterior arch of said vertebra;

where said first prosthetic facet is adapted to articulate with said second prosthetic facet.

9. A prosthesis according to claim 8 wherein at least one of said first fixation element and said second fixation element is a screw.

10. A prosthesis according to claim 8 wherein said first fixation element and said second fixation element are both screws.

* * * * *